US010477976B2

(12) United States Patent
North

(10) Patent No.: US 10,477,976 B2
(45) Date of Patent: *Nov. 19, 2019

(54) SUSPENDED BACK PILLOW FOR MAINTAINING A SIDE SLEEPING POSITION

(71) Applicant: Family Concepts II, LLC, Escondido, CA (US)

(72) Inventor: Vaughn W. North, Escondido, CA (US)

(73) Assignee: Family Concepts II, LLC, Escondido, CA (US)

(*) Notice: Subject to any disclaimer, the term of this patent is extended or adjusted under 35 U.S.C. 154(b) by 432 days.

This patent is subject to a terminal disclaimer.

(21) Appl. No.: 15/451,156

(22) Filed: Mar. 6, 2017

(65) Prior Publication Data
US 2017/0172308 A1    Jun. 22, 2017

Related U.S. Application Data

(63) Continuation-in-part of application No. 13/997,086, filed on Oct. 15, 2013, now Pat. No. 9,585,499, which
(Continued)

(51) Int. Cl.
A47G 9/10    (2006.01)
A47C 20/02   (2006.01)
(Continued)

(52) U.S. Cl.
CPC .............. A47C 20/027 (2013.01); A47G 9/10 (2013.01); A61B 5/02 (2013.01); A61B 5/11 (2013.01);
(Continued)

(58) Field of Classification Search
CPC ........................................................ A61F 5/56
(Continued)

(56) References Cited

U.S. PATENT DOCUMENTS 8,429,775 B2 *  4/2013  North ............... A47C 20/02
                                                128/869
8,720,447 B2 *  5/2014  North ................ A61F 5/56
                                                128/845
9,585,499 B2 *  3/2017  North ................ A47G 9/10

* cited by examiner

Primary Examiner — Tarla R Patel

(57) ABSTRACT

A device and method for enabling an individual located on a bed to sustain a side-sleeping orientation on either a left or right side. The device comprises a light weight, elongated back pillow having a longitudinal axis and being configured to assume a rest position at a back side of the individual and proximate to an adjacent surface of a bed when reclined in a side-sleeping orientation. The back pillow includes a hinge-like attachment structure which is positioned along a longitudinal edge of the pillow to secure the pillow to the individual's bed clothing. The attachment structure provides sufficient rotation to allow the pillow to rotate to the rest position in response to the force of gravity, ready to be engaged in a partial captured configuration between the individual's back and bed surface upon initial rotation of the individual from the side-sleeping orientation toward a supine sleeping position. Additionally, at least one front pillow is positioned and configured for concurrent positioning to a front portion of the individual at a knee and/chest location to complete a three-dimensional frame of reference for sleep position with respect to a bed surface and for developing an expectation within the individual's mind that the presence of the at least one front pillow indicates concurrent, probable presence of the back pillow capable of blocking rotation of the individual to a supine position.

20 Claims, 9 Drawing Sheets

Related U.S. Application Data is a continuation-in-part of application No. PCT/US2011/065933, filed on Dec. 19, 2011, which is a continuation-in-part of application No. 12/975,144, filed on Dec. 21, 2010, now Pat. No. 8,720,447.

(60) Provisional application No. 61/492,257, filed on Jun. 1, 2011.

(51) Int. Cl.
  *A61B 5/11* (2006.01)
  *A61B 5/145* (2006.01)
  *A61B 5/00* (2006.01)
  *A61B 5/02* (2006.01)

(52) U.S. Cl.
  CPC ........ *A61B 5/14542* (2013.01); *A61B 5/4806* (2013.01); *A61B 5/6892* (2013.01)

(58) Field of Classification Search
  USPC .... 128/846, 848, 871; 2/115, 125, 127, 133; 5/424, 630, 632, 655
  See application file for complete search history.

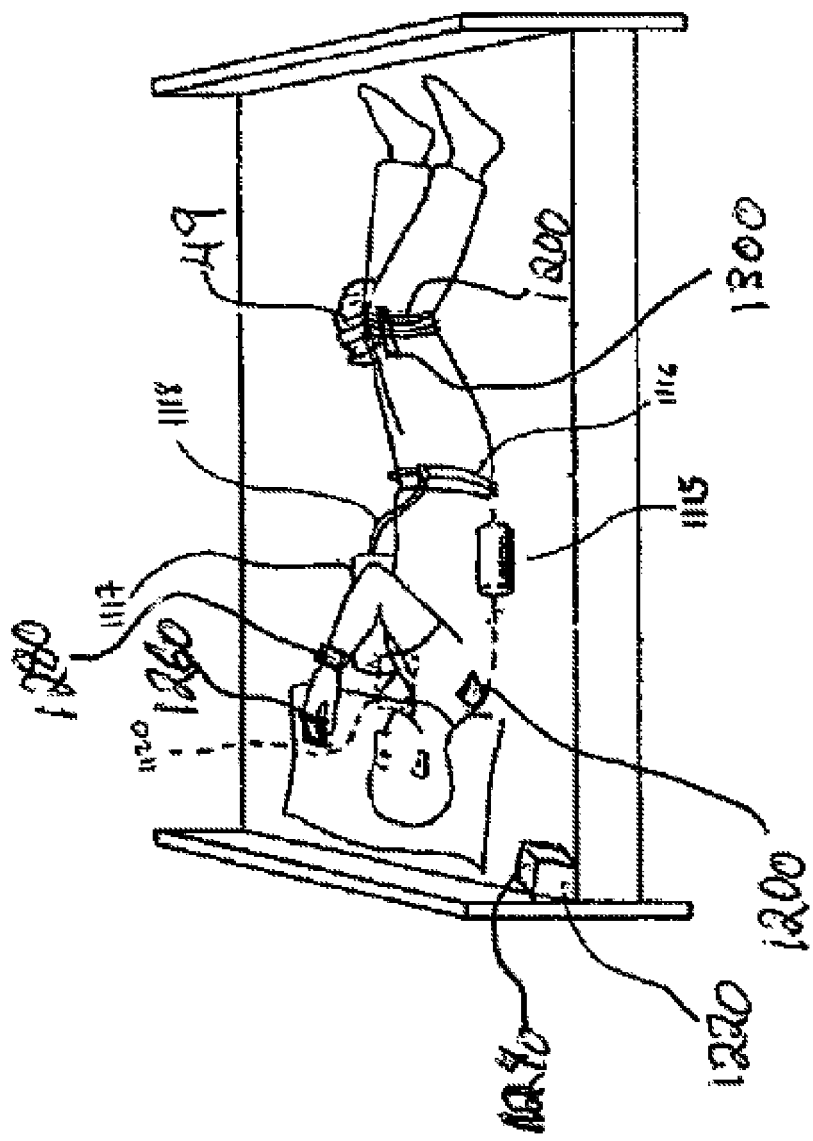

SUSPENDED BACK PILLOW FOR MAINTAINING A SIDE SLEEPING POSITION

This is a continuation in part application of U.S. application Ser. No. 13/997,086, filed Oct. 15, 2013, entitled Suspended Back Pillow for Maintaining a Side Sleeping Position which claims the benefit claims the benefit of International Patent Application No. PCT/US2011/065933, filed Dec. 19, 2011, which claims the benefit of U.S. patent application Ser. No. 12/975,144, filed Dec. 21, 2010, and U.S. Provisional Application No. 61/492,257, filed Jun. 1, 2011, each of which are incorporated by reference in their entirety herein.

TECHNICAL FIELD OF THE INVENTION

The present invention relates generally to a method and device for assisting a person to regulate sleeping positions during a semi-conscious or unconscious state, such as to remain on a side while sleeping and thereby avoid sleeping in a supine position.

BACKGROUND OF THE INVENTION

Sleep positional orientation may be an important factor for many persons in preserving health. For example, the typical dominant period of healing for the human body occurs during sleep Similarly, periods of illness or recovery often require additional rest that involves extended bedtime and sleep.

During times of sleep, semi-consciousness or unconsciousness, the position of the body is seldom within the person's conscious awareness. One may be changing positions among basic orientations of lying on one's back, left side, right side, and front. In addition, there are transitional positions between each of these basic positions (partially on back and left side, etc) that further define a near continuum of position orientations for the human body while in a bed-rest condition.

It is recognized that certain body positions may be preferred or even required during sleep and rest for effective health recovery and/or health maintenance. For example, persons having sleep apnea are more vulnerable to disruption of sleep when lying in a back or supine orientation, as compared to sleeping on a side. Similarly, individuals with a snoring problem may be less inclined to snore when in a side-sleeping position. In addition, relative physical positioning of parts of the body may be important, such as when one has a shoulder injury, spine misalignment, hip problem, etc. Even the process of aging may be affected by disposing the body in particular sleep or rest orientations that avoid stressing certain muscle groups and skeletal relationships. In short, a system or methodology of facilitating and controlling a more healthy positional orientation during sleep or rest would he beneficial.

SUMMARY OF THE INVENTION

The present invention is a device and method for enabling an individual located on a bed to sustain a side-sleeping orientation on either a left or right side. The device comprises a light weight, elongate, back pillow having a longitudinal axis and being configured to rest at a back side of the individual when reclined in a side-sleeping orientation on the bed. The back pillow includes attachment structure positioned along a longitudinal edge of the pillow to secure the pillow to the individual. The attachment structure provides sufficient flexibility to allow the pillow to bi-directionally rotate with respect to and rest against the individual's back to a laterally offset and suspended configuration in offset alignment with the individual's spine. At least one front pillow is provided and configured for positioning (i) at a knee as a knee pillow and/or (ii) at a front trunk location as a chest pillow for establishing at least three different points of contact reference to the individual in accordance with a Positional Orientation Sleep Aspect (POSE.) for providing a three-dimensional frame of reference for the individual during sleep.

A method is disclosed for using the elongate pillow and front pillows for maintaining a side-sleeping orientation for an individual alternately on either a left or right side as follows. The method includes attaching the light weight, elongate pillow at a back of the individual in a suspended configuration with respect to and substantially aligned with a spine of the individual, said suspended configuration including the hinge attachment including a rotational axis which enables the pillow to fall into contact at either a laterally offset left or right, hack side of the individual when the individual is lying on their respective left or right side. The individual's body is positioned in the side-sleeping orientation on the bed, allowing the pillow to rotate about the rotational axis to fall to near body contact with the individual which is (i) laterally offset from the spine, (ii) along the back side of the individual, and (iii) with the light weight pillow being proximate to the bed surface. At least one front pillow is applied at a knee and/or front trunk location for establishing at least three different points of contact reference to the individual in accordance with a Positional Orientation Sleep Aspect (POSA) for providing a three-dimensional frame of reference for the individual during sleep. Both the front and back pillows are used regularly by the individual during successive nights of sleep for a sufficient time to establish a subconscious expectation by the individual that the back pillow is in position to block supine sleep. Once established as a subconscious expectation, the back pillow can be eliminated, relying only on the at least on front pillow to provide an illusory impression of the three-dimensional frame of reference providing a psychological inhibition from attempting to rotate to a supine position.

Other objects and features of the present invention will be apparent to those skilled in the art from the following detailed description, taken in combination with the accompanying drawings.

BRIEF DESCRIPTION OF THE FIGURES

FIG. 16 illustrates the use of a forward tethered front or chest pillow in combination with the back pillow to simulate the dual pillow device without the intermediate member as part of a POSA sleep system.

DETAILED DESCRIPTION OF THE INVENTION

Figure 1:
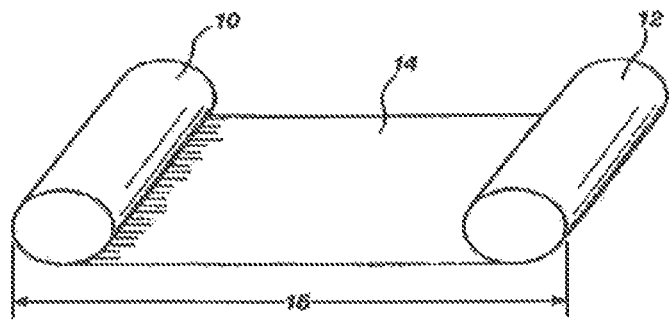
FIG. 1 illustrates a perspective view of a dual pillow system as disclosed in the parent patent application, including two opposing pillows tethered to an intermediate member.

The parent patent applications described a method and device involving a pair of opposing pillows tethered together in accordance with concepts represented by an invention referred to as Positional Orientation Sleep Aspect (POSA). Under normal circumstances, a person moves through various sleeping positions (right or left side and back or front) in a random manner. It is generally undesirable, therefore, to limit the body to one sleeping position such as may occur by simply imposing pillows snuggly at front and back sides of the individual in a restraining manner Although positioning a pillow at a single side of an individual can initially place the individual in a preferred side position, once the body moves away from the pillow, its positioning value is substantially compromised.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. In other words, something that is "substantially free of an item may still actually contain such item as long as there is no measurable effect thereof As used herein, the term "about" is used to provide flexibility to a numerical range endpoint by providing that a given value may be "a little above" or "a little below" the endpoint.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Positional Orientation Sleep Aspect (POSH) is a methodology and pillow system (FIG. 1) which helps a person achieve desired side sleeping positions without excessive restriction of movement. It utilizes an arrangement of pillows 10 and 12 having a limited width 15 and being coupled together by an intermediate member 14. This pillow system may be viewed as an ongoing sleep aid, or alternatively as a position conditioning tool as part of positional therapy, assisting an individual to form a new habit of sleeping on a side rather than in a supine position. As used in this application, reference to "side" will usually refer to a lateral portion of the individual's trunk, as opposed to the front and back of the individual. References to "front side" or "back side" should be understood to mean the front and back of the individual, as opposed to the lateral sides corresponding to the location of the arms.

A typical sleeping environment is a bed 20 (FIG. 2) which supports the body as a contact surface. This one-dimensional contact is acceptable during periods of being awake because the individual can simply make a mental decision to remain in the side-sleeping orientation. In a semi or subconscious state of sleep, however, the individual typically moves about without this mental awareness and is not able therefore to control a positional preference.

Over time, an individual may acclimate to various positional tendencies, such as sleeping on one's back, Unfortunately, those individuals having a habitual tendency to sleep on their back may find themselves more prone to snoring or other breathing problems such as sleep apnea. In these situations, the need to shift from sleeping on one's back to a side-sleeping orientation has been very difficult to achieve. Strategies have usually involved physically forcing the individual to assume the desired position. Specifically, the use of restraining pillows and devices compressed against the body that thereby block movement have often been required. Some sleep apnea patients have been encouraged to place a tennis ball or other stiff object on their back, to discourage a supine position. With methods involving the attachment of a ball or other stiff object to a central back location by pockets, straps or to a night gown or pajama top, physiological discomforts are inevitable when the object is captured under the back in a supine position.

With respect to the use of foam pad or other padded devices attached to the person's back, the user experiences discomfort from captured body heat or simply persistent contact of the object against his back while lying on one side. Although seemingly incidental at any given moment, prolonged contact over a large surface area or sustained weight against the back becomes the focus of mental awareness.

As mentioned above, the seemingly minor discomfort of a back-mounted device can also become a psychological irritant. For example, the weight of the object resting or hanging against the person's back in a side orientation may become distracting and annoying. After several minutes, even nominal pressure of the object may become significant and eventually very unacceptable. As a consequence, the individual may readily abandon the positional therapy. From an emotional or mental perspective, both the captured and suspended configurations of the object against the back simply become one more stress element that inhibits a relaxed state of mind for restful sleep.

Figure 5:
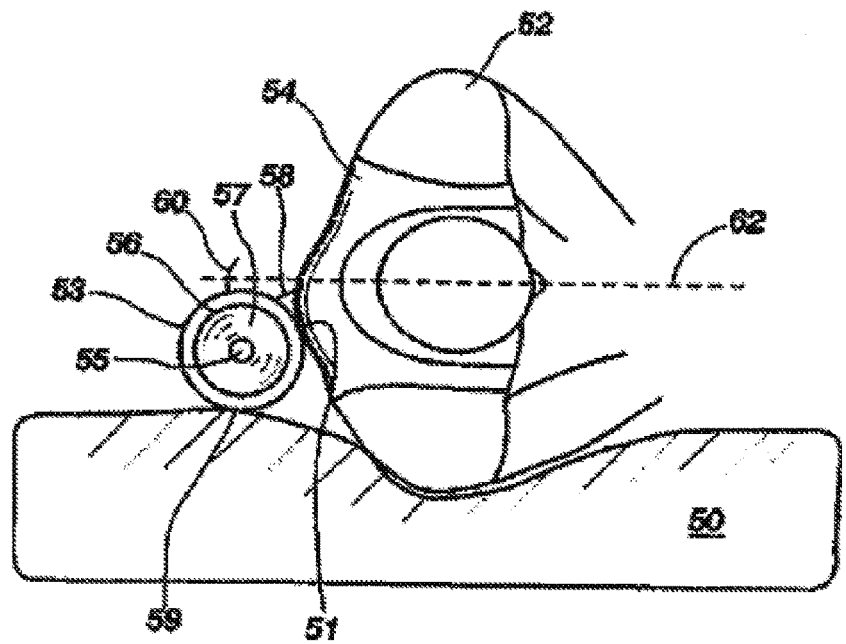
FIG. 5 shows a plan, top end view of the hack pillow illustrating a hinged configuration as part of a night shirt.
Figure 10:
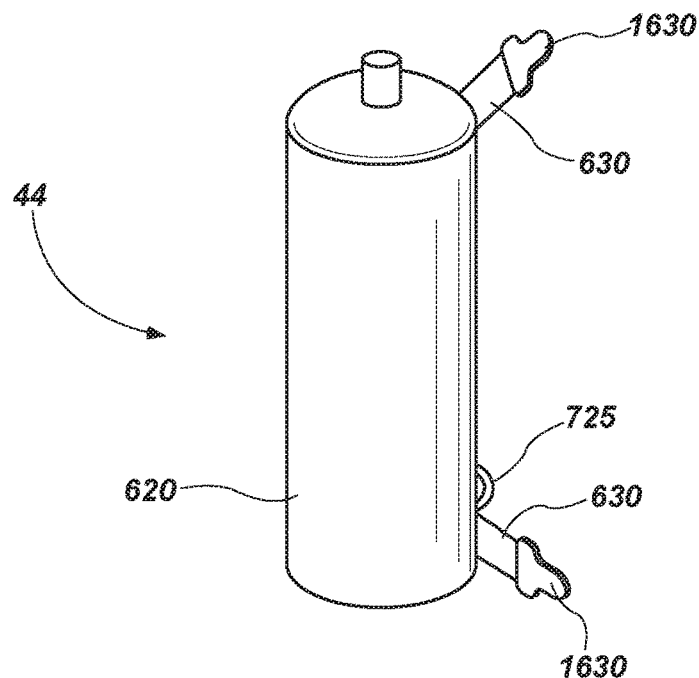
FIG. 10 is a perspective view of a suspended back pillow showing two attachment members having opposing angular orientations in accordance with one embodiment of the invention.

The present invention provides a combination of at least one or more front pillows to establish forward contact points of reference under POSA at the chest and/or knees while the hinge type back pillow structure assumes resting position on the bed which is neither fully captured nor fully suspended, but is supported at or very near the person's back while also resting on the bed surface as shown in FIGS. 5 and 10. This condition is referred to hereafter as "partial" capture of the pillow, in contrast to a full capture in which the person is lying on the pillow under his back (as in a supine or partial supine position). It is characterized by an absence of compressive or strong pressure on the back, yet sufficient contact to enable the individual to at least be aware of its presence when rotating toward a supine position. This partial capture reduces the contact irritation with the back as indicated above, while still blocking the individual from rolling to a supine position.

This concept can also be adapted to the POSA method as described in the parent applications for enabling an individual to mentally sustain a favorable inclination for a desired sleeping position rather than being physically forced to do so. This is accomplished in concurrent steps by developing a frame of reference for the mind and body based on a positional orientation sleep aspect (POSA). This is realized with a three-dimensional frame of reference to the body through appropriate contact points in a three-dimensional domain. Specifically, by establishing and maintaining at least two respective contact points at the forward and back sides of the individual, in addition to a third point of contact of the person on the bed surface, an increased mental awareness of the body's orientation can be sustained, despite the unconscious state of the individual during sleep.

The first point of reference (step a) in the POSA is contact of the trunk portion of the individual in the side-position orientation on the bed as shown in the figures. This naturally occurs based on the body being on the bed surface. Normally, this contact would extend along the length of the person, such as from the head, through the trunk and legs, down to the feet. This is referred to as a first reference point of contact, however, because it constitutes a single side of the individual. Because the present invention uses a pillow combination (FIGS. 1 and 2) comprising opposing first and second pillows 10 and 12 tethered between an intermediate member 14 positioned on the bed 20, the actual contact of the individual includes contact of a trunk portion of the body with the intermediate member 14 on the bed.

A second point of reference (step b) is contact of a back side 13 of the trunk portion with an adjacent side of the first pillow 10. This contact may be at the shoulders or hips, and any point there between. The nature of the contact arises from the stiffness and size of the pillow. The pillow needs to be sufficiently stiff to resist the weight of the body against it, yet soft enough to be comfortable to body contact.

It is desired that the pillow be sufficiently large in diameter to impede movement of the body over the pillow. Typically, at least a three inch diameter is desired; however, users have discovered that larger diameter pillows even in the approximate dimensions of 12×18 inches can be used as needed, particularly for obese patients. Individual preference is typically determined by balancing the minimal size needed to restrain movement of the user with the maximum size that can be managed conveniently for (i) pillow placement, (ii) maneuvering the individual to and from the pillow combination, and (iii) convenient storage of the device. A variety of sizes will be practical, when considering these minimum and maximum size considerations for different sized individuals.

The pillow also needs to be sufficiently stiff and resilient such that it does not overly compress under weight of the body and can thereby support and resist the second contact point of the POSA. Various pillow materials are available to meet this requirement and have been discussed in the parent application. inflatable bladders are particularly well suited for the pillow and include inflated air pillows or even balloons.

A further advantage of the inflated pillow is dissipation of body heat that is captured at the contact point of the pillow with the individual's back. An inflated pillow allows transfer of body heat to air or gas contained within the pillow and typically provides a more comfortable temperature environment for the user. In contrast, foam pillows, down inserts and other highly insulative materials can trap body heat and cause a person to sweat during the night. Finally, the air bladder offers the advantage of deflation. Specifically, it can be deflated for transport or storage and therefore offers the benefit of a smaller shipping or storage space.

A third contact reference point (step c) for POSA as described in the parent application includes contact of a forward projecting limb (arm or leg) of the individual with the second pillow 12. This contact may be with a knee 40, 42 in FIG. 3 or an elbow in a restraining configuration with the opposing pillows at maximum separation based on forceful resistance supplied by the fixed length of the thigh or upper arm, or a relaxed contact with less force between the second pillow and a lower leg or foot, and/or forearm or hand.

Figure 2:
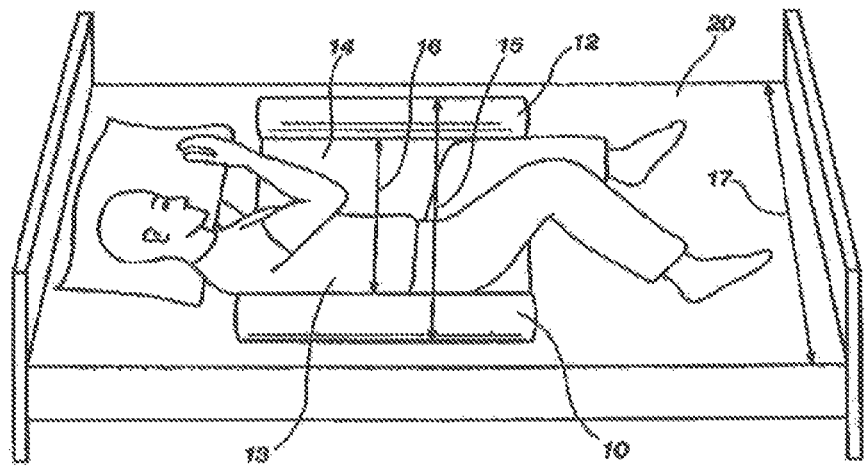
FIG. 2 depicts a graphic, perspective view of the invention in use on a bed with the pillow system fully extended.
Figure 3:
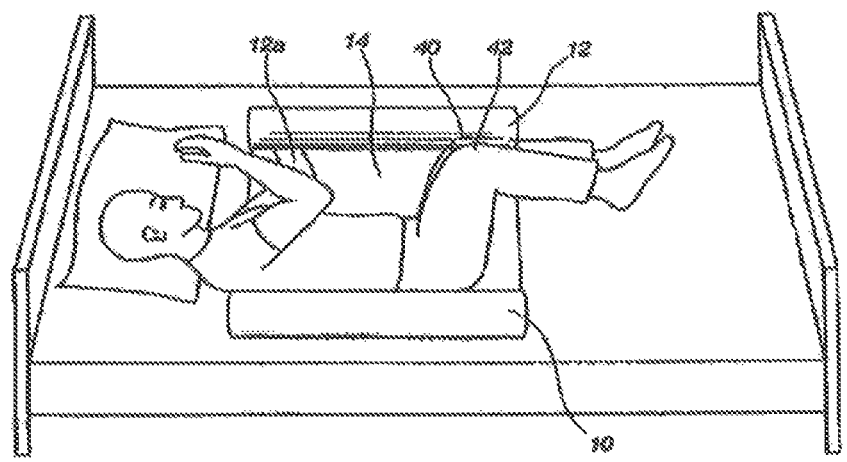
FIG. 3 illustrates in perspective an individual using the dual pillow system in a captured position between his knees.
Figure 4:
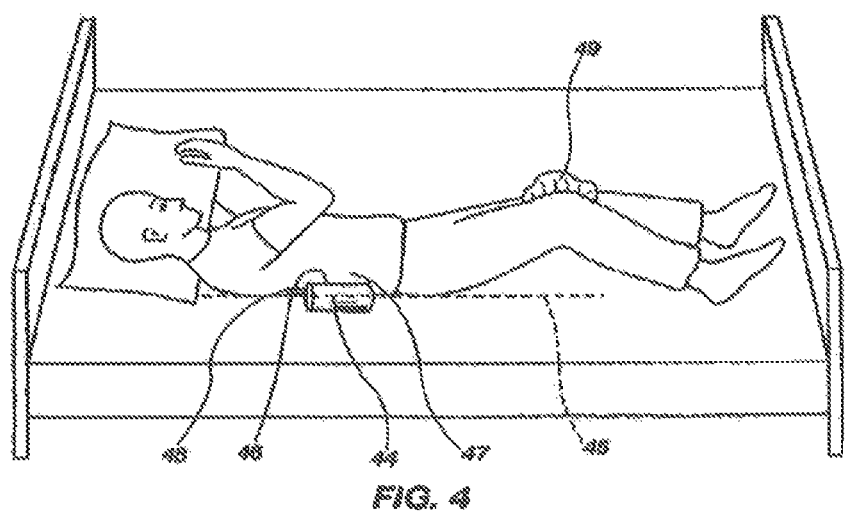
FIG. 4 represents a perspective view of a suspended hack pillow for limiting rotation of a person in bed from assuming a supine position.

FIG. 4 illustrates this third point of contact with a knee pillow 49, which has been shown to be particularly helpful after the person is conditioned to sleeping on their side with some form of knee contact 40/42 as illustrated in FIG. 3. In this embodiment, however, the person is using a back pillow 44 in combination with the knee pillow as a substitute for the dual pillow system of FIGS. 1-3. This is explained in detail hereafter.

Specifically, the parent application teaches that a person can become acclimated to sleeping on one side by maintaining the three points of reference of the POSA system during normal sleep. Over a period of time, this side-sleeping position can become a psychologically preferred position and may thereby actually work to the benefit of the user's health. The combination of back pillow and knee and/or chest pillow can thereby serve as a simulation of the full POSA system represented by FIGS. 2 and 3. Specifically, the mind and body respond to the contact at the back pillow 44, in combination with the pillow contact at the knees 49, such that the three points of reference are satisfied and the body perceives that it is in the preferred side-sleeping position. This can also be accomplished with a chest pillow 1117 as illustrated in FIG. 16, either alone or in combination with the knee pillow. The result is that the mind and body are both psychologically and physiologically satisfied within the POSA objective of having forward and rearward contact points as a frame of reference. In accordance with prior habitual side sleeping patterns realized within the dual pillow system of FIGS. 1 and 2, the user feels secure and remains on his side.

The advantage of the back pillow configuration is that it is much smaller and more comfortable to use. It also can function as a blocking pillow even if the individual moves laterally because the back pillow is attached to the individual rather than being stationary on the bed. Therefore, the back pillow follows the user and is ready to impede rotation to a supine position, where the back pillow of the dual pillow device stays in place on the bed. This continual presence of the attached back pillow adds a new feature within the POSA system, enabling the individual to perceive that the blocking pillow is "always" in place, even when it is not actually present. This is discussed hereafter with respect to FIG. 16. In essence, the person carries the positioning back pillow on his back without having to consciously manage its positioning or disposition as with the dual pillow system. Because of this, the individual is more likely to permanently continue the positional therapy of maintaining a side-sleeping orientation with the attendant benefits of improved cardiovascular health.

Figure 9:
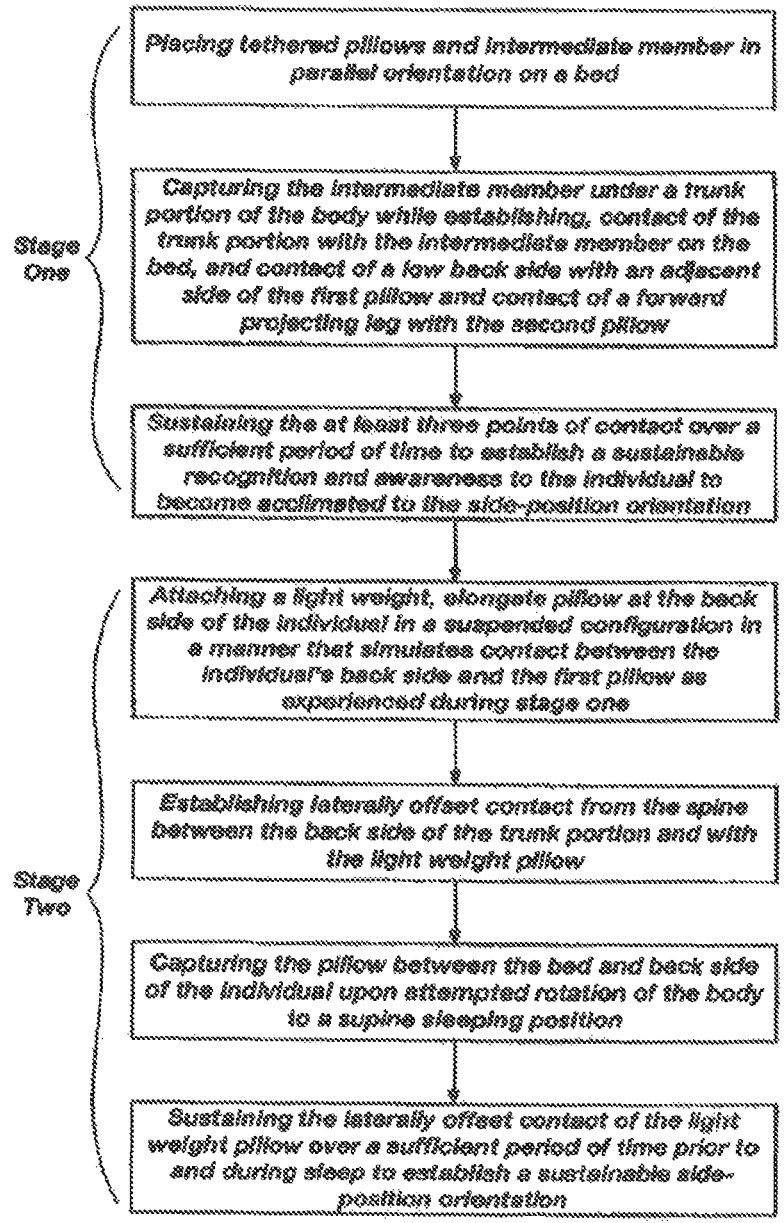
FIG. 9 illustrates one method of practicing the present invention.

Turning to the specific features and methods of the POSA system, FIGS. 1 through 3 illustrate steps a, b and c of the basic dual pillow system as used in the aforementioned POSA methodology. The method involves two stages as illustrated in FIG. 9 Stage one comprises steps a, b and c as set forth above for developing the three points of contact between the dual pillow. The user maintains this controlled side sleeping practice to reprogram the mind to expect the presence of the blocking pillow at the back, Stage one is implemented for the attached back pillow 44 by attaching the elongate back pillow 44 at the back side of the individual in a suspended configuration, with a longitudinal axis 45 of the pillow substantially aligned with the individual's spine and in a manner that simulates contact between the individual's back side and the first pillow 10. The individual's body is now in the preselected, side-position orientation on the bed and having prospective body contact laterally offset from the spine between the back side of the trunk portion 47 with the pillow, in this position, the user feels little or no pressure from the lightweight back pillow. Indeed, it is almost as if the pillow was not present. As the individual attempts to rotate backwards, however, the back pillow is then captured between the bed and backside of the individual, blocking the supine sleeping position. The user is protected from moving to a supine position, but enjoys a sense of freedom as if the back pillow was not being worn.

Reference to "laterally offset contact" relates to the relative position of back contact of the pillow 44 with respect to the spine and the bed surface when the individual commences rotation toward a supine position. Specifically, that portion of the back of the individual which is between (i) the side of the body lying on the bed and (ii) the back portion proximate to the spine is referred to as the "laterally offset" portion of the back along area 47 extending from the waist to the shoulder area. Corresponding positions would occur on both sides of the individual, to the left and right of the spine.

It should be noted in FIGS. 2 and 3 that the first pillow 10 contacts this laterally offset portion of the back or trunk of the individual when sleeping on a side. During, the process of positional therapy in the POSH method, the individual becomes accustomed to pillow contact in this region of the body during sleep. This laterally offset location may be simulated by the back pillow without need of the full, dual pillow system. The advantage of the attached back pillow is its ability to track with the individuals during lateral movement. If the user moves too far laterally from the first pillow 10 of the dual pillow embodiment, the blocking action may be compromised. On the other hand, the back pillow 44 will follow the individual during lateral movement and be ready to impede rearward rotation when needed.

Figure 11:
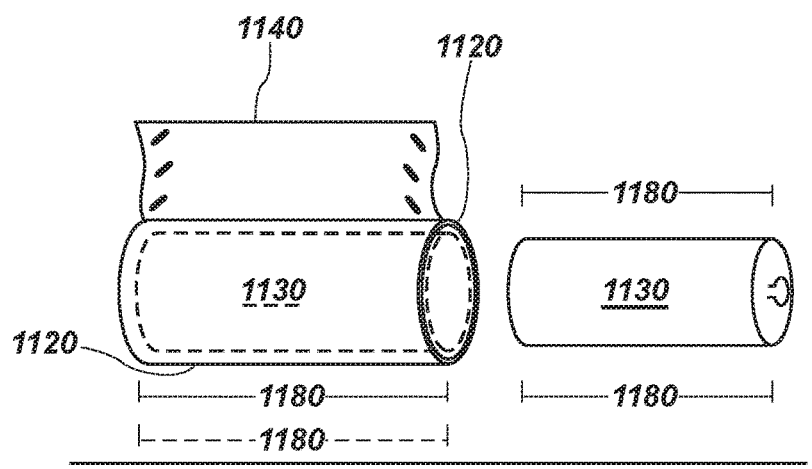
FIG. 11 illustrates a suspended back pillow having a substantially planar length configured to maximize the contact of the pillow with the surface of a bed or resting place.

As illustrated in FIG. 5 showing an individual 52 lying on a bed 50 on his right side, the back pillow 53 provides this contact when positioned in a similar manner and location as shown in the drawings. This occurs when the pillow 53 is essentially worn with the pajamas, tank top or night gown 54 or is otherwise similarly attached to the individual's body. This is accomplished by suspending the light weight pillow 53 from an attachment location by a hinge attachment member 58 extending from and generally parallel with the spine of the individual. This attachment member 58 may be a single connecting hinge 160 (FIG. 8), or a single sewn line of attachment between the shirt 54 and the pillow sleeve 56 which forms a rotational axis to the pillow. Similarly, the hinge structure can include several sewn lines of attachment between the shirt 54 and the pillow sleeve 56 which form a hinge member as shown in FIG. 11, in which case loose material of the shirt provides some slack between the shirt and pillow to allow a hinge-like rotation.

When attached at the this area, the pillow can then displace to either the right or left side, depending upon which side the individual selects as a sleeping side. Because of the attachment member's location 58 on the side of the pillow, the pillow body will hang down and in contact or near contact with both the appropriate back side of the individual and the bed surface 59. Reference to attachment at the side or along an edge of the pillow generally refers to attachment at a single edge of the pillow which preserves a hinge function to the pillow. The present invention favors such rotational hinge action in order to facilitate displacement of the pillow to opposing sides of the spine as the user turns between left and right side sleeping positions. Therefore, although an attachment strip 48 or 58 may have several locations of fixation to the pillow (sewing or adhesive, etc.) the strip itself represents a single attachment edge because it preserves the desired hinge function along an edge of the pillow.

The attachment member may be with a strip of Velcro®, snaps, fasteners, sewn fabric or any other convenient attachment means capable of coupling the pillow at the individuals back. In addition to supplying a key frame of reference contact 51 at the individuals back and thereby simulating the side-sleeping environment conditioned within the POSA methodology, the location of the back pillow impedes movement of the individual to a supine sleeping position. Because the pillow is attached at an edge of the cylindrical pillow body, it will hang under force of gravity toward the bed surface. This causes rotation of the pillow 53 and its longitudinal axis 55 downward and away from a central 62 or spine reference point, and into resting contact or near contact with the laterally offset portion of the individual's back 51, proximate to the bed surface. Typically, a portion of the bed clothing will fall downward with the pillow as illustrated, adjusting the pillow location even more toward the laterally offset back region as shown. When the individual attempts to roll into a supine position, the pillow is captured between the bed 50 and the laterally offset back portion at 51, blocking further rotation of the body. The fact that the back pillow can be in a near contact position prepared to block body rotation, yet at the same time be a non-irritant to the individual is a surprising improvement over prior art devices. Control of the precise location of the back pillow can be further facilitated by use of an adjustment strap attached to the pillow and around the waste of the individual, enabling the user to pull the strap laterally to position the back pillow as desired. This concept is the subject of U.S. Pat. No. 8,720,447 B2.

Another advantage of this invention occurs upon initial contact of the user with the pillow upon attempting to rotate into a supine position. When a light weight, balloon or inflated resilient pillow 53 is used as disclosed hereafter, the initial contact and resistance is very gentle, with the balloon component 57 within a sleeve 56 compressing slightly and avoiding an abrupt force on the individual's back. As the gentle contact intensifies with continued movement, the increasing resistance of the pillow is usually sufficient to urge the body back to a side-sleeping orientation without waking the person. Thereafter, the pillow again assumes its hanging or suspended configuration, lying near or against the laterally offset portion of the back.

A further benefit of the present invention arises with the hinge aspect of the attachment to the bed clothing or support band. With the pillow attached near the spine in a central location 62, the individual may shift from one side to another and the pillow will automatically gravitate to the appropriate right or left side, laterally offset location. Specifically, under force of gravity the pillow will fall between alternating and opposing laterally offset contact positions at the individual's back based on the side sleeping position selected—whether on the right or left side.

The pillow may include a two-piece construction with a sleeve member 140 having an interior open space 142 and configured in a desired shape suitable for the back pillow. The dimensions of the sleeve for an average sized person will typically be between six and eighteen inches in length, with a diameter of three to eight inches. The sleeve can be fabricated of flexible, light weight material such as polymer or natural fabric. A complementary attachment member 146 is formed along one edge of the sleeve for receiving the attachment member 152 of the body band. A balloon component 144 is positioned within the open space of the sleeve member and provides resilience to the pillow. Ideally, the balloon component conforms to the cylindrical shape of the sleeve when inflated. By using these materials, the pillow has a very low mass of less than 12 ounces, and ideally less than 5 ounces. A cotton fabric sleeve of 12 to 20 inch length and 4 to 12 inch diameter and an inflated interior balloon of common size was very effective and had a total weight of less than 2-10 ounces. With this light weight character, the user hardly notices the presence of the pillow at his back.

The following discloses a method of use comprising the steps of positioning the balloon pillow at the laterally offset portion of the individual's back and providing a gradual cushioned resistance response through gentle compression of the balloon component as the individual attempts to rotate to a supine position. In accordance with this method, the pillow provides (i) a gradual gradient increase of resistance against rotation of the individual to minimize discomfort while (ii) gently restoring the individual to the desired side-sleeping orientation. This gradual gradient increase commences at a null point of resistance so that the body is barely to register a sudden incidence of contact with the pillow. This gradient remains low to maintain a high level of comfort to the individual as contact pressure increases. By avoiding a sudden contact force when rolling to the supine position, the body appears to be able to generally register the contact and resume the side sleeping position without arousing or awakening the sleeper. This is accomplished by using a balloon component in which the skin of the balloon is very thin and remains pliable under pressure to conform to the body shape, based on a sufficiently low air pressure within the balloon. This is in contrast to other prior art structures having somewhat rigid outer skin structure that is less pliable and with which body contact serves to alert the individual of immediate contact.

Exemplary embodiments of the invention are disclosed hereafter, including descriptions filed as provisional and formal patent applications cited as priority documents.

Figure 6:
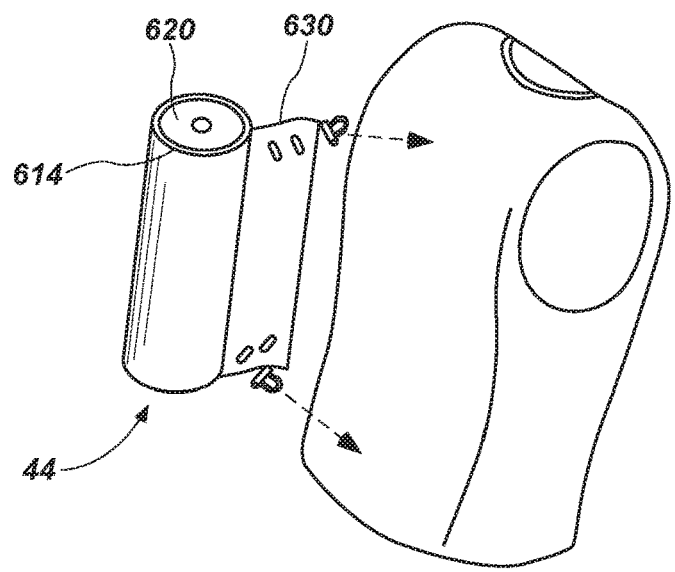
FIG. 6 is a perspective view showing a suspended back pillow with an attachment member and one or more attachment devices configured to removably couple the suspended back pillow on an individual's garment, in accordance with one embodiment of the present disclosure.
Figure 7:
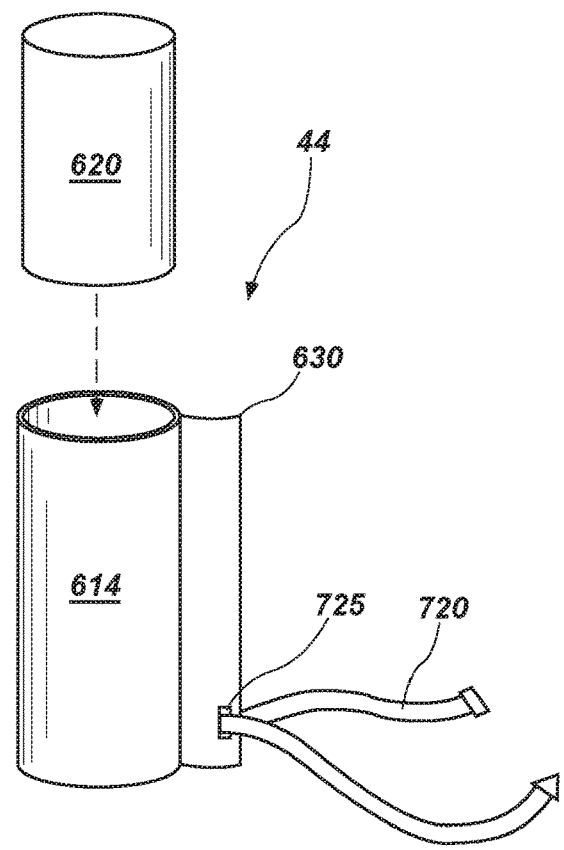
FIG. 7 represents a perspective view of a suspended back pillow for limiting rotation of a person in bed from assuming a supine position.

Illustrated in FIGS. 6 and 7, the suspended back pillow 44 includes a sleeve member 614 having a pillow element disposed therein 620. The dimensions of the sleeve member 614 may be between six and twenty five inches in length. Preferably, the dimensions of the sleeve member 614 are between nine and twenty inches in length. More preferably, the dimensions of the sleeve member 614 are between and eleven and fifteen inches in length. A hinge component 630 allows the pillow to be separated from continual contact at the back of the individual, thereby avoiding uncomfortable pressure on the user's back. The length of the hinge component or attachment structure 630 defines the extent of displacement permitted for the pillow from the user. This will be a function of the trunk size of the individual, as well as the softness of the bed. A preferred length of the hinge and tab structure is such that the pillow will rest in contact with both the user's back and the adjacent bed surface.

These factors have been fully disclosed in the parent applications and will he further explained hereafter. In short however, the pillow with attached hinge permits a variety of pillow positions with respect to the user, including positions that have a very light, almost imperceptible contact at the person's body, as well as strong compressed contact such as occurs when the pillow is resisting a supine sleeping position. In addition, the hinge and tab enable the user to shift fully away from contact with the pillow, allowing a new level of comfort as if the pillow were not attached. The pillow can he pushed away by the user's hand or by rotating the trunk, thereby leaving the pillow in a rest position on the bed surface (sustained in the rest position by a frictional exterior surface on the sleeve). Nevertheless, the short length of the tab maintains the pillow within an operating distance proximate to the individual's back, thereby preventing the supine sleeping position. It will be appreciated that by rolling slightly away from the pillow, a separation gap of several centimeters can give total relief from the contact irritation of the pillow on the skin of the user. in summary, the pillow design embodies a combination of features that provide a surprising new level of comfort and control to the use of a back pillow, including features that eliminate many of the long existing negative aspects previously associated with efforts to prevent supine sleep positions. This construction also enables the individual to acclimate to the back pillow as if it were not present, by acting only when engaged upon rotation toward a supine position. As mentioned hereafter, this function will allow the user to become conditioned with an expectation that the back pillow will block rotation (even though not present), provided other POSA contact points trigger the perception of a presumed back pillow being attached.

Returning to the sleeve construction, in one embodiment, the sleeve member 614 is fabricated from a coarse or rough material. The coarse or rough material may include those materials that provide a measure of resistance to the sleeve member 614, such that when the exterior surface of the sleeve member 614 is pressed against a surface, such as a bed sheet, the sleeve member 614 resists sliding across the surface. Some non-limiting types of rough or coarse fabrics may include various types of suede material such as passion suede, rhino suede, micro fiber suede, and so forth. Other types of fabrics may include various types of velvet, polyester, cotton, and/or multiple combinations of various types of fabrics.

The purpose of the frictional surface or friction generating surface is to steady the pillow position with respect to the user. It is designed to stay in a resting position, except when the pillow needs to function as part of the positional therapy. This may be to prevent the pillow from inadvertently sliding away from the individual's back as the person starts to roll toward a supine position. Or also, it may be that the individual wants to shift his body away from the pillow to escape continual contact with the pillow surface. With a frictional surface the pillow will tend to remain in place or be captured between the back and bed surface as a blocking element against rolling onto the back, as was explained in the parent application.

Illustrated in FIG. 7, the suspended back pillow 44 can include a securing strap 720 configured to extend around the waist of a user. Because the pillow is attached to a pajama, shirt or garment, it is possible for the garment itself to migrate around the trunk of the individual, causing a shift in position for the pillow to one side or the other. Typically, the night shirt is pulled somewhat snuggly around the torso to limit such migration. If needed, however, a securing strap 720 can be securely attached at a lower end of the sleeve and positioned around the torso to stabilize the pillow in a centered configuration on the back of the user. In one non-limiting example, the securing strap 720 is embodied in a belt 720. This can also function as an adjustment device for laterally moving the pillow left or right as needed to properly position the pillow in contact or near contact with the user as desired. This is accomplished by merely grasping the belt at the user's front and pulling to the side to shift the belt and attached back pillow left or right.

It is contemplated that the belt 720 may be coupled and/or removably coupled to the suspended back pillow 44. In the illustrated example, the belt 720 is removably coupled to the attachment member or hinge component 630, More particularly, the belt 720 extends through a slot 725 at the base of the attachment member 44. In at least one aspect the belt 720 can function to secure the suspended back pillow 44 at centered position on a user's back, such as near the spine. Securing the suspended back pillow 44 near the spine can be particularly advantageous as in many instances when the user's garment tends to migrate while a user sleeps. This migration can in some cases, shift the position of the back pillow 44 to a less effective position at the user's side. When the Shown in FIGS, 6 and 7, the sleeve member 614 includes an attachment structure, member, or tab 630, the attachment member 630 configured to attach the sleeve member 614 or pillow 620 to the garment of an individual. The attachment member 630 is formed at one edge of the sleeve member 614 to enable attachment to the user's garments or bed clothing, forming a suspended configuration suitable to realize the desired a partial capture at the juncture of the user's back and bed surface, as described in more detail in the parent U.S. patent application Ser. No. 12/975,144. In this position, the pillow has minimal contact at the individual's back because most of the weight of the pillow rests on the bed surface. Nevertheless, it remains in position adjacent to the back to resist rolling movement of the individual to a supine position.

In one embodiment, the attachment member 630 can be readily formed by having extra material and/or fabric extend beyond the sealed perimeter of the sleeve member 614 prior to fabrication, leaving this flat, uninflatable section to form the attachment member 630 as shown. Alternatively, in the absence of a sleeve member 630, it is contemplated that the attachment member 630 may be directly attached to the pillow or inflatable element 620

It is contemplated that the length of the attachment member 630 may be selected to fit the specific size of the user. Greater lengths will he needed for a larger physical frame in order to properly position the pillow at the partial captured location as described in more detail in shown in the parent U.S. patent application Ser. No. 12/975,144. In various embodiments, such lengths may extend form one quarter inch to several inches as needed to position the pillow at the rest position on the bed, adjacent the individual's back. In still another embodiment, the length of the attachment member may be about half of an inch to five inches.

In an alternative embodiment, a more specific adjustment of length can be accomplished by selecting one of the attachment points that are included in the attachment member 630 as the point of attachment to the bed clothing or user's garment. It is contemplated that the one or more attachment points can be disposed on a variety of locations on the attachment member 630. In one non-limiting example, the one or more attachment points can be disposed along the upper end and bottom end of the attachment member 630. In one aspect, having multiple attachments points along both the upper and bottom end provides a user with options to adjust the length of the attachment member 630.

Figure 8:
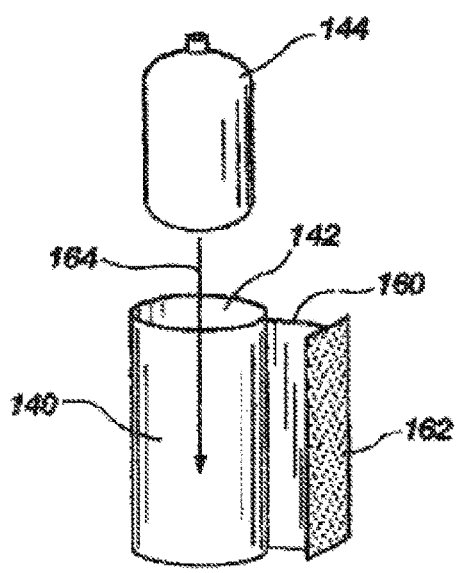
FIG. 8 is a perspective view of a pillow sleeve with attached hinge member illustrating insertion of a balloon member for inflation therein.

FIG. 8 illustrates an alternate form of attachment which includes a flexible, light weight hinge component 160 coupled to the pillow sleeve at one side and to the attachment member 162 on the other side. The material composition of the hinge member is preferably thin and flexible to provide for unimpeded rotation of the pillow and its elongate axis 164 with respect to the spine. The length of the hinge component may extend at least a quarter inch from the pillow edge but at no greater length than will allow the pillow to fall to the laterally offset contact position at the individual's back based on the individual's size, providing an extended radius of rotation to the pillow member to position the pillow to a suspended rest position in contact with the individual's back and proximate to the bed.

For example, an individual of average size may have require a hinge member of only up to one inch in length, whereas a person of very large stature may need a greater length, depending upon the diameter of the pillow and softness of the mattress on the bed. It will be apparent that a soft mattress will allow the person to sink into the mattress body, increasing the proximity to the suspended pillow and thereby decreasing the length of the hinge member. Ideally, the pillow should fall to an initial position in contact with the individual's back and in slight contact with the bed surface. If desired, the user may then slightly shift position to form a small displacement gap between the pillow and back. Accordingly, the back pillow may require tailoring in size to the body dimensions of the user in order to properly function as disclosed, resulting in the desired "partial" capture of the pillow between the laterally offset back area and the bed when the individual attempts to rotate to a supine position.

With the hinged embodiment, the pillow will hang lower towards the bed and may apply slightly more contact pressure at the user's back than is acceptable, particularly if partially captured between the bed and offset back area. This can readily be resolved by the user reaching behind the back and releasing the captured pillow from between the bed and back side of the individual by slightly tilting or displacing the pillow away from the back to a "partial" captured, resting position on the bed. Although there may be a slight contact at the offset back side, the nominal weight of the pillow is substantially unnoticeable when it is resting primarily on the bed. Accordingly, this last step provides a static, non-supine sleep condition with nominal contact pressure by the pillow on the individual for maximum comfort.

FIG. 9 outlines exemplary methods associated with various embodiments of the invention. More particularly, the method and figures illustrate the sequential use of the suspended back pillow subsequent to use of a dual pillow system described herein. It has now been discovered that this same methodology can be accomplished without the use of the dual pillow embodiment, wherein the stage two procedure is the only method applied to train the individual under the POSA system. This can be implemented by use of the combination of back pillow and chest and/or knee pillow combination as disclosed herein, maintaining a period of continuous use until the subconscious of the individual becomes acclimated to an illusory expectation that the hack pillow is in place because of the presence of the other pillow or pillows at the front of the individual. This method is described in greater detail hereafter.

Shown in FIG. 10 is a suspended back pillow 44 according to one exemplary embodiment of the invention. In this embodiment, the hack pillow 44 includes a first and second attachment structure or hinge component 630. These hinge components 630 are composed of a material with either a straight or slanted orientation such that closer rotation of back pillow 44 to the individual can be maximized. The hinge components may be coupled to the sleeve member 614 or directly to the pillow 620.

It is contemplated that a variety of methods and attachment devices 1630 may he used to removably couple the attachment member 630 to a user's garment. In one non-limiting example, shown in FIG. 10, the attachment device 1630 can include a clipping member 1630 configured to removably secure the attachment member 630 to a user's garment. The clipping member 1630 may he any type of suitable attachment device 1630, such as but not limited to clips, buttons, pins, grasps, and so forth. It is contemplated that the clipping member 1630 can be coupled to the attachment member 630 in a variety of ways. For example, the clipping member 1630 can be stitched and/or fastened the attachment member 630.

In another example, the clipping member 1630 can be attached at the one or more attachment points, each attachment point including a slot extending through the attachment member 630. The slot can be sized to enable a user to insert the end of the clipping member therein.

As mentioned above, the attachment structures or members 630 can be oriented at an angle that opposes the attachment member 630 at the opposing end of the pillow 44. In one non-limiting example, as shown, the attachment members 630 are oriented at opposing angles of about forty-five degrees. This reduces the likelihood that the clips 1630 could be captured between the pillow and user's back, causing discomfort from the clip.

In at least one aspect, orienting the attachment members 630 at opposing angles increases the distance at which the attachment member 630 is removably secured to the garment. This increases the separation distance at which the attachment member is secured to the garment providing stability to the securement of the attachment member 630 to the garment. Furthermore, increasing the distance at which the attachment member 630 is secured to the garment can function to provide tension across the length of the pillow 44, thereby improving the hinge function of the attachment member 630 across a user's back.

Also shown in FIG. 10, a securing slot 725 can be coupled to the pillow 44 or sleeve member 614. The securing slot configured to enable a user to utilize a securing strap 720, as described herein.

FIG. 11 is a perspective view of a sleeve member 1120 having a pillow element 1130 disposed in the interior of the sleeve member 1120. As described in the various embodiments herein, the sleeve member 1120 includes an attachment member 1140. In a more specific embodiment, the pillow element 1130 includes a substantially fully inflated inflatable element, as described herein.

Illustrated in FIG. 11, the substantially straight front length of the sleeve member 1120 is advantageous and provides a greater surface area of the sleeve member 1120 that can contact the surface of a bed 1150. Increasing the surface area of the contact point of the sleeve member 1120 can assist a user in maintaining a side-sleeping position by assisting to prevent movement of the suspended back pillow when a user attempts to move on his or her back during sleep. Specifically, the frictional surface prevents the user's body from pushing the pillow across the bed surface and away from the user's back. Instead, the stable pillow remains in place and is captured between the user's back and the adjacent bed surface. The gentle resistance of the inflated pillow resists the movement of the body, but does so with a gentle gradient of resistance as disclosed in the parent patent application. This added comfort helps to keep the person in a sleeping state, rather than awakening them with an abrupt and abrasive resistance that can be painful. Furthermore, the increased surface area of the front length of the sleeve member 1120 can function to distribute the force caused by the weight of the user on the suspended back pillow as the user attempts to move on his or her back during sleep. This distribution of force can function to further increase a user's comfort while using the suspended back pillow.

Also shown in FIG. 11, there is a pillow element 1130 having opposing lengths at the exterior surface of straight or flat configuration. As shown, the opposing lengths are defined as being substantially flat at the edge 1180 to conform to the structure of the sleeve 1120 and corresponding straight edge.

While the pillow, or inflatable element 1130 illustrated in FIG. 11 includes a pair of opposing lengths having a substantially planar definition, it is contemplated that the pillow, or inflatable element 1130 may include a singular length having a substantially planar front length or definition.

Figure 12:
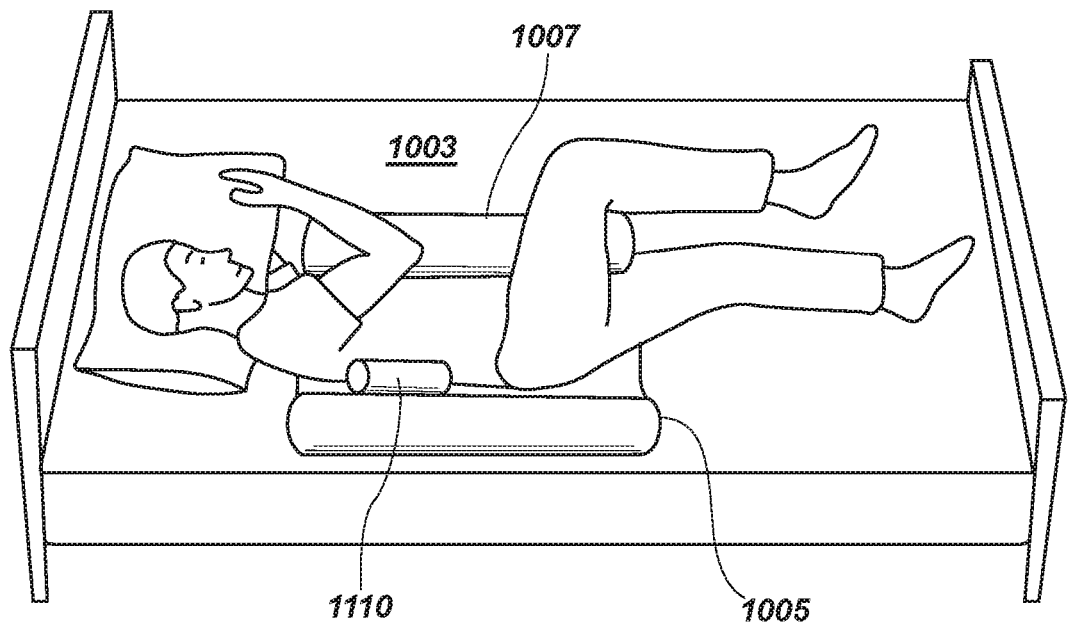
FIG. 12 illustrates the concurrent use of both a back pillow and a dual pillow device for increased side sleep control, in accordance with one embodiment of the present disclosure.

Although the present disclosure has described use of the hinged back pillow as a singular device, it is important to note that it may be used in conjunction with the dual pillow system as described in the parent application. Specifically, FIG. 12 illustrates an individual 1001 positioned on a bed 1003 between two opposing pillow members 1005 and 1007 of a dual pillow device. The dual pillow device provides increase control to the user by giving front and back side points of reference. Persons having extreme tendencies to move to a supine position may be benefited by using the back pillow and dual pillow device as a system. As shown, the individual 1001 has a back pillow 1110 positioned in accordance with the present disclosure. The back pillow 1110 is restrained in its displacement by the adjacent pillow 1005 of the dual pillow device. The combined pillows prevent the individual from inadvertently assuming a supine position by rotating during sleep. Although this combination is clearly more restrictive of the desired freedom of movement as previously discussed in the parent application, individuals with severe conditions may need the greater restriction to meet the needs of their sleep problem.

Figure 13:
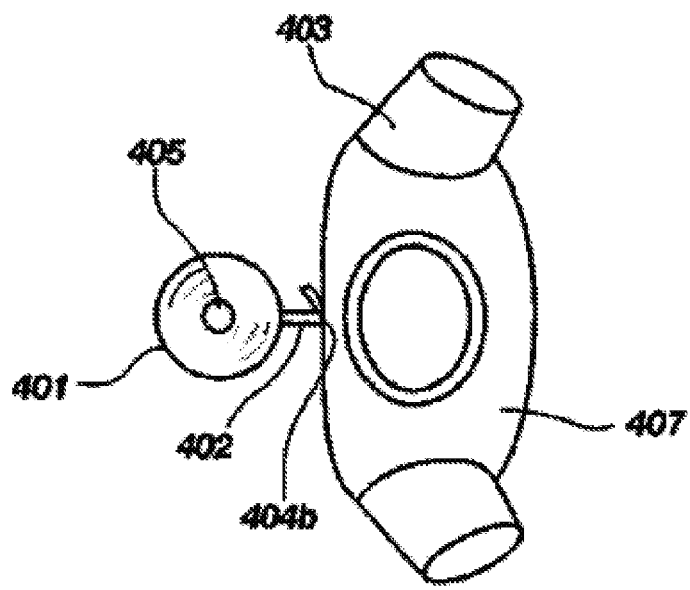
FIG. 13 shows a top plan view of the embodiment of the present disclosure attached to a shirt.
Figure 14:
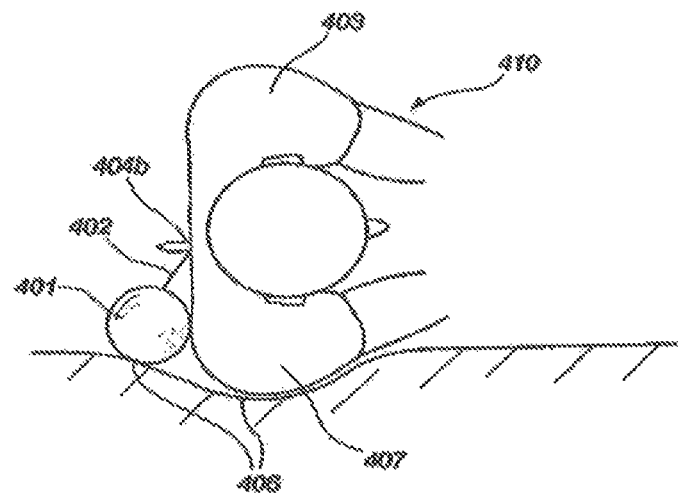
FIG. 14 illustrates a top plan view of the shirt and back pillow of FIG. 13 in use on a bed surface.

Shown in FIGS. 13 and 14, the back pillow can comprise an air bladder component 401. The air bladder component for the back pillow comprises a cylindrical, inflatable pillow member with an appropriate fill valve 405 to enable the user to blow into the pillow to inflate to a desired pressure level. If desired, the valve can include a quick release mechanism to allow rapid deflation where this would be appropriate. Such a deflation option would be even more appropriate on the dual pillow embodiment where an individual may need rapid egress from the bed without having to crawl over an inflated, elongate pillow.

An attachment tab 402 may be formed on the pillow member or on the sleeve member. The length 408 of the tab may be selected to fit the specific size of the user. A more specific adjustment of length can be accomplished by selecting one of indexed markings along the length of tab 404 as the point of attachment to the bed clothing. For example, FIG. 13 illustrates shirt 407 with a point of attachment of the tab 402 at index mark 402b. This selection could be based on positioning the unattached pillow 401 in the proper configuration of "partial capture" as shown in FIG. 14, then while holding the pillow in place, extending the tab 402 upward to the location of the user's spine to identify the correct tab length. The index markings 404b can be used as a reference to identify the proper point of attachment, sized precisely to the user's frame. Once determined, the tab can be sewn, pinned, clipped or otherwise affixed to the bed clothing at the index mark, such as 404b. As shown the proper partial capture configuration depends upon the frame size and weight of the individual 410, the indentation of this person into the mattress 406 and the circumference of the pillow 401.

Figure 15:
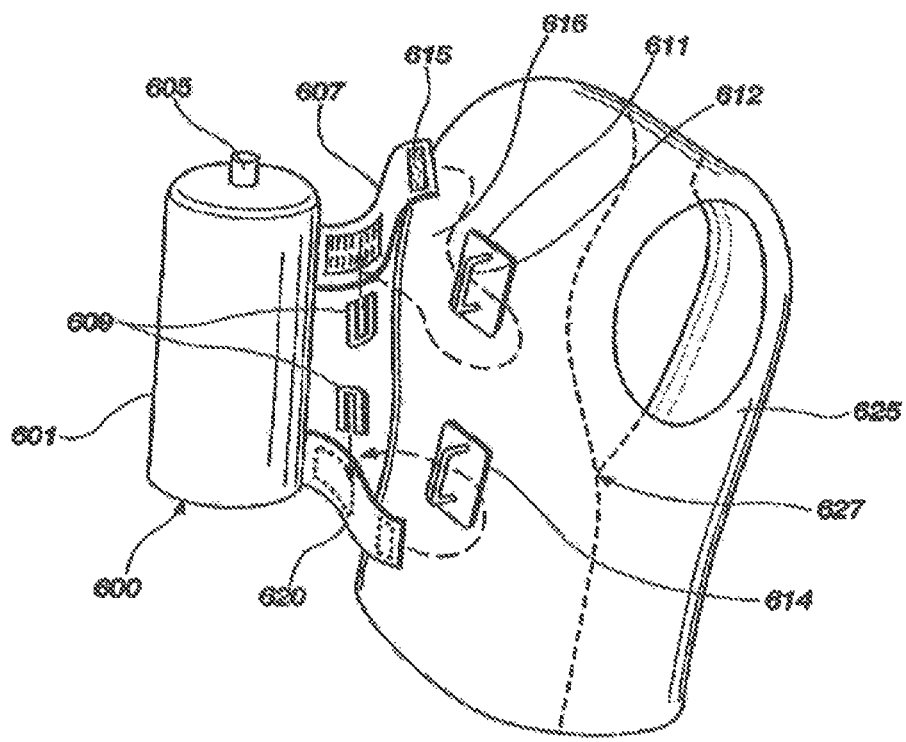
FIG. 15 provides a perspective view of a vest embodiment of the present invention.

FIG. 15 illustrates a vest-type embodiment which offers greater stability in positioning the back pillow on a stable platform at the user's back. The pillow 600 is similar in construction to the previous pillows illustrated and includes s cylindrical body 601 and fill valve 605. Straps 607 and 620 will be used to attach the pillow to mounting loops 611 and 614 on the back of the vest. The same positioning steps can be applied as described above, with the straps 605 and 620 being adjusted in length by fastening the loose end through loop opening 612 and attaching it to the interior section of the strap 616 with Velcro or other fastening means. The user then tests the positioning of the pillow in the side position on the bed, snaking further adjustments in the length to optimize the position. The vest 625 can be comfortably fastened in the front to retain this configuration through the night.

In order to implement the independent use of the hack pillow, the present invention contemplates a method for maintaining a side-sleeping orientation for an individual alternately on either a left or right side which comprises the steps of :

a) attaching a back pillow at the back of the individual in a suspended configuration with respect to and substantially aligned with the individual's spine, said suspended configuration including a hinge attachment function which enables the pillow to fall into contact at either a laterally offset left or right, back side of the individual when the individual is lying on their respective left or right side;

b) positioning at least one front pillow at a knee and/or front trunk location for establishing at least three different points of contact reference to the individual in accordance with a positional orientation sleep aspect (POSA) for providing a three-dimensional frame of reference for the individual during sleep;

c) initiating rotation of the individual's back toward the suspended pillow and toward a supine position;

d) impeding displacement of the pillow along the bed surface and away from the individual's back during rotation;

(e) partially capturing the back pillow between the bed and lateral back side of the individual while maintaining contact at the front side of the individual with at least one front pillow, thereby blocking full rotation to the supine position; and;

(f) regularly repeating this method during successive nights of sleep for a sufficient period of time to establish a subconscious expectation by the individual that the back pillow will be in a position to block supine sleep positions.

Specific reference was made in the parent application to use of a knee pillow in combination with the back pillow. It should also be noted that the ability of the individual to maintain a positional awareness sleep aspect (POSA) can be simulated without the need of a dual pillow system. This is illustrated by the combination of FIGS. 12 and 16. It is accomplished by having the individual's back against the back pillow 1115 and by attaching front or chest pillow 1117 at a forward location of the individual such as at the knees in FIG. 9. This attachment may be by means of clips 1119 attached to bed clothing as discussed above, or with the use of a tether line 1118 tied to a waist belt 1121 or at another body location. In this manner, the front pillow 1117 operates as a knee pillow 1117 or front contact pillow to provide the opposing points of reference as discussed for POSA. An individual that has trained himself to sleep with this POSA element can simulate the side sleeping environment by using the pair of independent and unconnected pillows 1115 and 1117 similar to how the opposing connected pillows work in a dual pillow system with connected front and back pillows.

FIG. 16 illustrates how the front pillow 1117 can be repositioned at will by the user to other desired locations. In the illustrated. embodiment, the user has pulled the pillow 1117 upward to a chest location. The tether line 1118 gives the user immediate access to the pillow wherever the pillow may be located, even if the pillow has been displaced from contact with the individual. With the front pillow at the chest location, the combination of front 1117 and back 1115 pillows very nearly mirrors the connected dual pillow operation of the parent application. With contact at both front and back sides, the individual is filly aware of his or her side sleeping orientation and feels secure and safe. If desired, an individual can also position the pillow at his or her neck as illustrated in phantom line 1120. In this position, the pillow can restrain the jaw from undesired movement during sleep, as well as provide the front contact position for POSA.

Also shown in FIG. 16, the tether line 1118 can include be coupled to a waist securing member 1116 or belt member 1116. The belt member 1116 can be any type and/or kind of suitable belt member configured to be secured around a portion of a person's body, such as the waist, arm, and so forth. The belt member 1116 can include securing elements such as buckles, loops, and so forth configured to secure the belt member 1116 around an individual. It is contemplated that the present disclosure includes one or more methods for manufacturing and providing a suspended back pillow 100 and all the elements described herein.

It is contemplated that the inflatable element may be manufactured from a variety of rubber type materials, such as but not limited to neoprene rubber, silicone rubber, natural gum rubber, santoprene rubber, and so forth. Alternative suitable elements for the inflatable element can include PVC, latex, polyesters, nylons, and various polyesters have various types of laminates such as thermal polyester laminates. It is contemplated that an inflatable element can have a range of thickness, such as 0.01 mm to 1 mm and from 1 mm to 0.05 mm.

It is contemplated that the inflatable element and/or pillow element described herein can be manufactured from a variety of materials such as but not limited to vinyl types, polyester types, nylon, and so forth. Such materials can additionally include: a variety of rubber types, latex, nylon, polyurethane material, and so forth. Furthermore, in one embodiment, it is contemplated that the suspended back pillow may be embodied in a single pillow insert, the pillow insert having an attachment member coupled thereto and/or extending therefrom as described herein, In this manner, a sleeve member is unnecessary as the pillow insert can be attached directly to the garment of an individual via the attachment member extending from the pillow insert.

Actual user studies have confirmed the effectiveness of both the dual pillow and back pillow configurations in enhancing an individual's ability to remain in a side sleeping position during sleep. Some persons have noted that after several weeks or months of use, the inclination to rotate to a supine position has been substantially or even completely eliminated. This suggests that certain individuals may be more prone to development of subconscious positional recognition as proposed by the POSA methodology. Some individuals may have a more aggressive inclination toward seeking a supine sleeping position. Applicant's experience using just the back pillow demonstrated this tendency.

Following an extended period of use for over two years of the combination of back pillow 44, knee pillow 49 and chest pillow 1117, applicant has discovered that the POSA 3-dimensional reference frame has produced an unexpected result. Specifically, training with the POSA system with both a back pillow and front pillow 49 and 117 appears to create an enhanced subconscious memory of the combination of pillows which can then function to block rotation, even though the back pillow may have been removed. In other words, applicant has discovered that by continuously using the front (chest or groin) pillow and/or the knee pillow in combination with the back pillow, the body appears to eventually presume that the hack pillow is also in place, even if absent. Accordingly, there is little or no tendency to rotate to the supine position.

To confirm that the two front pillows had the effect on their own of inhibiting supine sleep, a formal sleep study was performed at the Scripps Sleep Clinic at the Green Hospital in La Jolla, Calif. in September 2016. In this study, no back or front pillows were used. In the absence of any front or back pillows, the sleep study revealed an approximate three equal division of sleeping time on the back, the left side and the right side. In other words, the body experienced random movement to the supine, right and left sides when no pillows were present. In subsequent experiments by applicant where only the chest and knee pillows were involved, the body was inclined to avoid supine sleep. This result suggested that the presence of the front pillows did indeed have an inhibiting effect toward supine sleep, despite the fact that no back pillow was in place that would otherwise restrain rotation to the supine position.

To follow up on this unexpected experience, CPAP use was included nightly by applicant to determine the occurrence of apnea events which would indicate that supine sleep had occurred. Typically in applicant's experience, any degree of supine sleep would typically result in 5 to 15 apnea events per hour as registered on the CPAP. When no pillows were used in the experimental activities, apnea events occurred as expected, at 5-15 events per hour. In other words, without either back or front pillow support, the natural inclination of the body was to randomly include supine sleep.

However, if the chest and knee pillows were used (even without a back pillow), the apnea readings for the night were negligible. This clearly suggests that the chest and knee pillows alone were inhibiting supine sleep. The preliminary conclusions from this experience indicate that repeated use of the POSA system, preferably using the back pillow in combination with the chest and knee pillows, develop an enhanced subconscious memory that continues to presume the presence of a back pillow, despite the fact that the back pillow is not actually in place.

It may well be that the hinged back pillow, which allows the user to position it at the individual's back without actual body contact, trains the body to refrain from rotating to supine positions in view of the inevitable blocking action of the pillow upon rotation. This is possible because the back pillow is usually not applying pressure at the individual's back. During side sleep, the pillow is lying next to the individual but may often not even be noticed. This unique ability to disconnect from the body creates the sensation that the pillow is not present.

Accordingly, the mind and body do not actually "feel" the pillow present, but simply learn to expect to encounter the pillow upon rotating toward a supine position. Over time, the body becomes acclimated to the blocking function of the back pillow, in combination with the other points of contact at the chest and knee. Therefore, with the chest and knee pillows in place, it appears that the mind presumes that the back pillow will also be in place without actually feeling it in contact. Once this expectation is realized, the user is therefore able to avoid having to use the back pillow by simply using the chest and/or knee pillows alone. This constitutes an unanticipated training function of the original POSA methodology dealing with conditioning the body to avoid supine sleep.

Referring to FIG. 16, this concept can be stated as a method for training a user to be restrained from supine sleep by repeatedly and concurrently sleeping with (i) a back pillow 1115 including a hinge component positioned at the user's back for allowing free fall of the pillow to right and left sides in a partially captured position between the user's back and an adjacent bed surface, and (ii) a chest pillow 1117 in contact with a front trunk and/or arm portion of the user to develop an associated awareness of the combination of both the back pillow and chest pillow as an effective pillow combination to restrain the user from supine sleeping positions. It should be noted that the presence at both front and back positions of the individual's trunk develops a broad, stabilizing platform that gives an increased sense of comfort and security against rearward rotation during sleep.

After repeated use of this combination of back and chest pillows, the individual may become conditioned to the expectation of a blocking back pillow during sleep. When the subconscious mind of the individual reaches an expectation (even if illusory) of the expected blocking action associated with the back pillow, the side sleeping position can become second nature to the individual. In other words, the user is able to withdraw the back pillow when acclimated to the expected restriction against the supine position caused by the effective pillow combination of both back and chest pillows. The user thereafter feels inhibited from moving to the supine position because of memory and expectation of the back pillow and its blocking function, despite an actual absence of the back pillow at the user's back.

This phenomenon offers a distinct advantage for use of the present invention. Specifically, an individual may be able to eventually be free of the inconvenience of wearing a back pillow during sleep, relying soley on the mental expectation that supine sleep will be blocked based on use only of a front pillow. For most individuals, cradling a front pillow at the chest is simply reminiscent of holding a teddy bear as a child. This is usually not an uncomfortable experience. Ironically, use of the chest pillow as a cradled object now becomes an effective tool for creating the illusory expectation that a back is also in place, thereby inhibiting the mind from triggering rotation to the supine position. Applicant's experience with an aggressive inclination toward supine sleep requires periodic renewal of actual blocking action by the back pillow. Accordingly, an individual may need to reinstate the illusory back pillow perception by actually wearing the back pillow on occasion.

In addition to use of the POSA system for inhibiting supine sleep, the present invention is well suited for adjunct use with various sleep monitoring devices. Referring again to FIG. 16 for example, a warning device 1200 can be attached to the individual for detecting the supine position of the body. After a predetermined period (1-3 minutes for example) the individual would feel a mild shock or vibration or hear an audible alert to encourage arousal and repositioning to a side sleeping orientation. One skilled in the art could select from a number of vibrators, current generators, audible emitters, etc., to enable an appropriate warning. These could be integrated within a smart watch 1280 or otherwise attached to the body. Such a device, in combination with the present hinged back pillow system, is ideal because it is occasionally possible for the pillow to shift too far off to the side and fail to effectively block the user from supine positions. A back up system of warning the individual of supine sleep allows quick correction and repositioning of the back pillow. On the other hand, an individual may simply want to rest momentarily in the supine orientation, knowing, that this would only be allowed for several minutes. Going beyond the predetermined time allowance of 1-3 minutes would result in the appropriate triggering of the alarm notification.

Similarly, the use of a remote orientation monitor 1220 coupled to the warning device 1200 which is capable of maintaining an ongoing record of sleeping positions would allow the user to track the effectiveness of the POSA pillow system. This can be used in combination with a CPAP instrument or other device that can then be coordinated with occurrence of apnea events. Here again, numerous orientation measuring devices are well know and could be readily adapted to use with the present pillow system.

Similar adjunct devices could include a snoring monitor 1240 integrated with the orientation monitor 1220, an oxygen monitor 1260 mounted on a finger or ear lobe and/or wrist cardiac monitor 1280 associated with the pillow system or as separate device to be used by the individual for gathering relevant sleep data. An inertial detector 1300 mounted on a knee pillow or to the user's leg would be useful for indicating the presence of restless leg syndrome and other movement-based sleep disturbances known in the art. Such adjunct devices and systems are intended to be illustrative of the ability of the present pillow invention to include comprehensive monitoring and assistance to the individual seeking improved sleepy and are not to be considered limiting.

Other sleep assist methods, structural features and combinations thereof will become apparent to one of ordinary skill in the art, based on the foregoing examples. Accordingly, the present invention is to be construed by the following claims, and is not to be limited to specific examples provided above.

The invention claimed is:

1. A method for maintaining a side-sleeping orientation for an individual alternately on either a left or right side which comprises the steps of:
   a) attaching a back pillow at the back of the individual in a suspended configuration with respect to and substantially aligned with the individual's spine, said suspended configuration including a hinge attachment function which enables the pillow to fall into near contact at either a laterally offset left or right, back side of the individual when the individual is lying on their respective left or right side;
   b) positioning at least one front pillow at a knee and/or front trunk location for establishing at least three different points of contact reference to the individual in accordance with a positional orientation sleep aspect (POSA) for providing a three-dimensional frame of reference for the individual during sleep;
   c) initiating rotation of the individual's back toward the suspended pillow and toward a supine position;
   d) impeding displacement of the pillow along the bed surface and away from the individual's back during rotation;
   (e) partially capturing the back pillow between the bed and lateral back side of the individual while maintaining contact at the front side of the individual with at least one front pillow, thereby blocking full rotation to the supine position; and;
   (f) regularly repeating this method during successive nights of sleep for a sufficient period of time to establish a subconscious illusory expectation by the individual that the back pillow will be in a position to block supine sleep positions with the actual use of the at least one front pillow.

2. A method as defined in claim I, comprising the additional steps of g) refraining from attaching the back pillow while maintaining contact of the at least one front pillow during sleep to determine if the subconscious illusory expectation that the back pillow is present is able to inhibit rotation of the individual to a supine sleeping position and h) repeating this additional step until the individual is able to remain in a side sleeping position without the use of the back pillow.

3. A method as defined in claim 2, comprising the additional step of replacing the back pillow with a small, non-blocking object capable of creating a physical impression of the presence of an actual back pillow to enhance the illusory expectation that rotation toward a supine position will be blocked.

4. A method as defined in claim 2, further comprising the concurrent use of two front pillows positioned at the knee position and the front trunk position.

5. A method as defined in claim 1, wherein the illusory expectation of presence of the back pillow arises because of repeated actual blocking of rotation of the individual to a supine position a sufficient number of times in association with actual presence of the at least one front pillow, thereby creating a perception that a detected presence of the front pillow confirms likely presence of the back pillow as well.

6. A method as defined in claim 1, further comprising the step of cradling a chest pillow in contact at the front trunk while concurrently using the back pillow to block rotation of the individual to a supine position, thereby creating a broad stability platform to sustain a side sleeping orientation.

7. A device for enabling an individual located on a bed to sustain a side-sleeping orientation on either a left or right side, said device comprising:
   a light weight, elongate pillow having a longitudinal axis and being configured to rest at a back side of the individual when reclined in a side-sleeping orientation on the bed, the elongate pillow including a hinge attachment structure to secure the elongate pillow to bed clothing of the individual, said attachment structure having a rotational axis and a longitudinal edge attached to the elongate pillow with an orientation in general alignment with a spine of the individual and having sufficient flexibility to allow the elongate pillow and its longitudinal axis to bi-directionally rotate in opposite directions in response to gravity to rest against a backside of the individual at a laterally offset, partial captured contact position and in contiguous concurrent contact with an adjacent bed surface, while the individual remains in a side-sleeping orientation; and
   at least one front pillow configured for positioning (i) at a knee as a knee pillow and/or (ii) at a front trunk location as a chest pillow for establishing at least three different points of contact reference to the individual in accordance with a Positional Orientation Sleep Aspect (POSA) for providing a three-dimensional frame of reference for the individual during sleep.

8. A device as defined in claim 7, further comprising both the knee pillow and the chest pillow configured for positioning at both the knee and front trunk locations.

9. A device as defined in claim 7, wherein the knee pillow further comprises an attachment strap for retaining the knee pillow in a position between opposing knees of the individual.

10. A device as defined in claim 7, wherein the chest pillow is sufficiently large to allow the individual to cradle the chest pillow in an upper am in a side sleeping position.

11. A device as defined in claim 7, wherein the chest pillow includes an attached tether line for securing the chest pillow to the individual in a location proximate to the individual's front trunk.

12. A device as defined in claim 7, further comprising a position orientation measurement device configured for attachment to the individual for determining orientation of the individual's body during sleep.

13. A device as defined in claim 7, wherein the orientation device includes a recording component for keeping a record of body position orientations of the individual during sleep.

14. A device as defined in claim 7, further comprising a position orientation device that includes a warning component for alerting the individual when the individual's body has been in a supine position for a predetermined period of time.

15. A device as defined in claim 7, wherein the warning component includes a vibrator configured to gently arouse the individual to enable repositioning to an alternate orientation from the supine position.

16. A device as defined in claim 7, wherein the warning component includes a circuit for generating an electric current at the individual's skin configured to gently arouse the individual to enable repositioning to an alternate orientation from the supine position.

17. A device as defined in claim 7, further comprising a snoring monitor for detecting and recording snoring activity by the individual during sleep.

18. A device as defined in claim 7, further comprising an oxygen monitor for detecting and recording low oxygen levels in the individual's blood during sleep.

19. A device as defined in claim 7, further comprising an inertial detection monitor for detecting and recording sudden movements of the individuals body during sleep, including detection of restless leg syndrome.

20. A device as defined in claim 7, further comprising a heart monitor for developing a record of cardiac activity during sleep.

* * * * *